US008900120B2

(12) United States Patent
Lewis et al.

(10) Patent No.: US 8,900,120 B2
(45) Date of Patent: Dec. 2, 2014

(54) STIMULATION DEVICE

(75) Inventors: Adam Lewis, London (GB); Julia Margo, London (GB)

(73) Assignee: The Pleasure Works Limited (GB)

( * ) Notice: Subject to any disclaimer, the term of this patent is extended or adjusted under 35 U.S.C. 154(b) by 83 days.

(21) Appl. No.: 13/558,394

(22) Filed: Jul. 26, 2012

(65) Prior Publication Data

US 2013/0030245 A1 Jan. 31, 2013

(30) Foreign Application Priority Data

Jul. 28, 2011 (GB) .................................. 1113000.2

(51) Int. Cl.
*A61F 5/00* (2006.01)
*A61H 19/00* (2006.01)
*A61H 23/02* (2006.01)

(52) U.S. Cl.
CPC ........... *A61H 19/00* (2013.01); *A61H 23/0254* (2013.01); *A61H 2201/165* (2013.01)
USPC ........................................................... 600/38

(58) Field of Classification Search
USPC .................................. 600/38-41; 601/46, 84
See application file for complete search history.

(56) References Cited

U.S. PATENT DOCUMENTS 6,338,721 B1 * 1/2002 Lebecque ....................... 601/71

FOREIGN PATENT DOCUMENTS

WO WO 01/34028 * 5/2001

* cited by examiner

*Primary Examiner* — John Lacyk
(74) *Attorney, Agent, or Firm* — Barnes & Thornburg LLP

(57) ABSTRACT

Presented is a device comprising a vibratory means which applies vibrations of a controllable and adjustable amplitude and frequency to the frenulum of the male genitalia, the vibratory means not requiring the user to hold it in place during use, and wherein the vibratory means are further adapted to apply vibrations to the female genitalia during use.

10 Claims, 1 Drawing Sheet

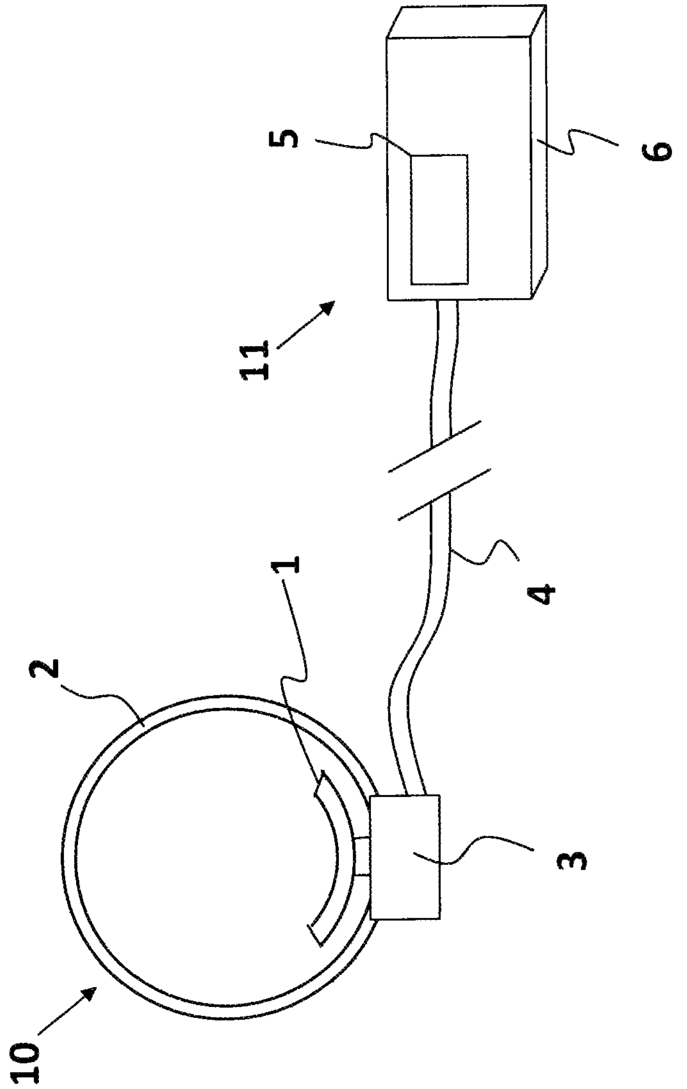
1
2
3
4
5
6
10
11

STIMULATION DEVICE

The present invention relates to a device which provides simultaneous stimulation of the male and female genitalia. More specifically, the invention relates to a lightweight device, which when attached to the penis and held against the vagina, delivers (variable vibration to the frenulum and clitoris There are a wide variety of devices which are already available which seek to stimulate the male genitalia through a variety of means, either for medical purposes, such as sperm collection or to assist those suffering from erectile dysfunction, or simply for pleasure.

A large range of products has been developed and marketed with a recreational purpose, what are commonly referred to as sex-toys. These devices seek to stimulate the male genitalia in order to give pleasure. In these circumstances, an important aim of these devices is the stimulation and arousal. Often postponing the orgasm is desirable. Various different means of stimulation have been proposed in the past, offering the man varying degrees of control and requiring different levels of intervention and action by the man.

The male sex toy market is extensive but lacks variety. Despite the fact that it is know that vibration applied to the penis can cause arousal and result in orgasm and ejaculation, there are relatively few products which are actually designed to stimulate the penis through vibrations. The majority of male sex toys are 'sleeves' which fit over the penis and are moved by hand.

Some products do work by applying vibration, but these are either not adjustable or they fail to offer the optimum amplitude of vibrations, focusing instead on frequency. What is more, the vibrations delivered are often too low in amplitude to be effective for the majority of men.

Products designed to be hands-free do not offer optimum vibratory amplitude and are not adjustable. They are also designed to fit around the base of the penis, neglecting the frenulum. Vibrating cock rings are also invariably designed to fit around the base of the penis.

The frenulum is the most sensitive area of the penis and it has been found that vibrations applied to this small area of the penis is very effective in causing arousal and orgasm.

Medical research has identified the required vibratory amplitude and frequency for stimulating the penis. The study reported by N. L. Brackett in Human Reproduction Update (1999) Vol. 5, No. 5, p 551-552 discusses the use of different amplitude and freucny of vibration in order to produce ejaculation in patients with spinal cord injury. The results suggested that vibration having a frequency of about 100 Hz and an amplitude of about 2.5 mm is suitable for causing ejaculation in patient with spinal cord injuries. The study showed that both high and low amplitude vibrations were successful in causing ejaculation, frequently within just two minutes. This is useful in a medical setting, such as the study in question, but does not represent an optimum result for a device which is designed for recreational use.

Evidence suggests that the optimum amplitude and frequency of vibration for the purpose of pleasure varies from person to person and may also vary during use of the device. It is therefore an objection of the present invention to provide a device which is easy to use, requires minimal manual action by the user but which allows extensive control and adjustment by the user, in order to allow the experience to be controlled.

SUMMARY OF THE INVENTION

According to a first aspect of the present invention, a device is provided comprising a vibratory means which applies vibrations of a controllable and adjustable amplitude and frequency to the frenulum of the male genitalia, the vibratory means not requiring the user to hold it in place during use, and wherein the vibratory means are further adapted to apply vibrations to the female genitalia during use.

In a second aspect of the invention, a method is provided for stimulating the frenulum of the male genitalia for pleasure, the method comprising using a device according to the first aspect of the invention.

In a third aspect of the invention, a device is provided which comprises a textured underside which is designed to be positioned against the female genitalia to apply vibrations to the clitoris and vagina. Accordingly, embodiments may provide dual stimulation (i.e. simultaneous simulation to both a female and a male user) by means of vibration.

Embodiments may have the following attributes:

1. Hands-free
2. Can be used when the penis is still flaccid
3. Adsapted to stimulate the frenulum
4. Provide adjustable amplitude and frequency
5. Battery powered, so cheap to maintain
6. Compact and lightweight so easily transported.
7. Adapted to stimulate the clitoris and/or vagina.
8. Adapted for use as a dual stimulator of the both the frenulum of a male user and the clitoris of a female user.

BRIEF DESCRIPTION OF DRAWING

FIG. 1 is a schematic drawing of a device according to the present invention. The drawing is not to scale.

DETAILED DESCRIPTION

The present invention relates to a simple and easy to use stimulatory device which allows the user to control the amplitude and frequency of the vibrations applied to the frenulum and/or the vagina or clitoris, whilst being an essentially hands-free device, so that a user does not have to manually hold or manipulate the device during use.

In one embodiment of the invention, a vibrating surface is provided, which transmits the vibrations produced by the device to the frenulum. The surface may be a flat surface or it can be concave, to receive the shape of the penis and sit comfortably against the frenulum during use. Where the vibrating surface is concave, this can also help to minimise movement of the vibrating surface relative to the frenulum during use.

The vibrating surface is preferably formed from a material which has one or more of the following properties, and most preferably all of them: easy to clean; hypoallergenic; not heat conducting.

In one embodiment, the vibrating surface will be a plastic material. In an alternative embodiment, the vibrating surface may be made from a more malleable or pliable material, such as a gel, which transmits vibrations but which is also soft and may shape itself, to an extent, to the shape of the surface of the penis. Suitable materials will be well-known to a skilled person.

The device of the present invention is intended to be a hands-free device and to be easy and comfortable to use. As the device is attached to the penis during use, the size and weight of the part of the device which is held against the frenulum should be as small as possible. Ideally, the vibrating surface is, at most, only slightly larger than the area of the frenulum. The vibrating surface should not be so small that any small movement during use could render it less effective due to poor positioning.

The vibrating surface is held in place against the frenulum by a holding means. The holding means is preferably one or more adjustable straps. The straps are preferably elasticated and may be fitted when the penis is flaccid and which extend sufficiently to maintain the position of the vibrating surface with increasing tumescence of the penis. The straps may be provided with a coating which makes them relatively non-slip, to prevent movement of the vibrating surface relative to the frenulum during use.

The use of an elasticated strap has the advantage that it will become tighter as the user's erection progresses, thereby pushing the vibrating surface on to the frenulum with increasing force. This can improve the effect of the vibration.

In alternative embodiments, the holding means may be one or more adhesive patches which are adhered to the penis and hold the vibrating surface in place.

The vibration is produced by a motor. This will preferably a small and light motor capable of producing vibrations of variable frequency and amplitude. The frequency of vibration produced is preferably up to 150 Hz, more preferably up to 110 Hz. The amplitude of the vibration produced is preferably up to 3 mm, more preferably up to 2.5 mm.

The motor is controlled by a control panel, allowing the user to adjust the frequency and the amplitude of the vibration produced. Preferably, the control panel is separate from the motor and can be easily accessed and used whilst the device is in use. In a preferred embodiment, the control panel is attached to the motor by a wire which allows the control panel to be conveniently located during use of the device. In an alternative embodiment, the control panel may be totally detached from the motor, providing "remote control" of the device.

The device of the invention is preferably battery operated, although it could be main powered. The battery is preferably located away from the motor and the vibrating surface, so as to minimise the size and weight of the part of the device to be attached to the penis. In one embodiment, the battery is connected to the motor by a wire, optionally like the control panel.

It would be particularly convenient for the battery to be a rechargeable battery, with the device having a charger or a charging station to allow it to be charged between uses.

In a further embodiment, the device is comprised of a textured underside which is shaped to stimulate the female genitalia. The material of the textured underside may be a malleable or pliable plastic or silicone or other material which transmits vibrations from the vibrating platform.

In another embodiment vibrations may be delivered to the underside via a separate or twin motor. Thus, in such an embodiment, vibrations supplied to the frenulum (via the vibrating surface) may independent from vibrations applied to the clitoris (via the textured underside). Further, such separate vibrations may be independently controlled. Vibrations to the underside may therefore be controlled by a separate control panel.

In anther embodiment the material of the underside may be ridged, moulded, or designed to fit inside the vagina.

In another embodiment, the material and shape of the underside is designed to magnify vibrations from the vibrating platform For a fuller understanding of the invention, reference is now made to the accompanying drawing, which is intended to be an example of one possible embodiment of the invention described and claimed herein and is not intended to be limiting.

The device is made up of a vibrating part 10 which is to be attached to the penis during use, and a control part 11 which is made up of the control panel and houses the battery or batteries.

The vibrating part 10 comprises a vibratory surface 1, which is held in place by a holding means, the adjustable elasticated strap 2. The vibration is produced by a small, light motor 3 which is connected by a wire 4 to the power supply 6 and control panel 5 which make up control part 11 of the device.

In use, the vibrating part 10 of the device is attached to the penis (which may be flaccid or erect), using the adjustable strap 2. The device is positioned so that the vibrating surface 1 is against the frenulum and the strap is adjusted so that the device is held in place and is comfortable for the user. The concave shape of the vibrating surface makes the correct positioning easier, as it is designed to complement the shape of the penis. The concave shape can also assist in keeping the part in position during use, as the shape will limit relative movement between the vibrating surface and the penis.

Once the vibrating part has been attached, the user may either hold the control part of the device or position it for easy access if required. The device may be switched on and the amplitude and frequency can be adjusted to offer a personalised and varied experience.

The invention claimed is:

1. A device comprising a vibratory means which applies vibrations of a controllable and adjustable amplitude and frequency to the frenulum of the male genitalia, the vibratory means not requiring the user to hold it in place during use, wherein the vibratory means comprise:

one or more motors capable of producing vibrations of variable frequency and amplitude;

a first vibratory surface adapted to be vibrated by the one or more motors and to contact the frenulum during use; and a second vibratory surface adapted to be vibrated by the one or more motors and to contact the female genitalia during use, and wherein the vibratory means are arranged such that vibration of the first vibratory surface may be independent from the second vibratory surface.

2. A device as claimed in claim 1, wherein the vibratory means is adapted to be held in place against the frenulum during use by an adjustable strap.

3. A device as claimed in claim 1, wherein the first vibratory surface is concave and shaped to receive the penis.

4. A device as claimed in claim 3, wherein the first vibratory surface is made from a malleable material which transmits vibrations and whose shape can be moulded.

5. A device as claimed in claim 1, wherein the frequency of vibration is up to 150 Hz.

6. A device as claimed in claim 1, wherein the amplitude of the vibration is preferably up to 3 mm.

7. A device as claimed in claim 1, wherein the frequency and amplitude of vibration is controlled by a control panel.

8. A device as claimed in claim 7, wherein the control panel is separate from vibratory means.

9. A device as claimed in claim 1, wherein the device is battery operated.

10. A method for simultaneously stimulating the male genitalia and female genitalia for pleasure, the method comprising using a device according to claim 1.

* * * * *